United States Patent [19]

Daftary et al.

[11] Patent Number: 5,290,171
[45] Date of Patent: Mar. 1, 1994

[54] UNIVERSAL CARRIER FOR CARRYING VARIOUS ANATOMICAL DENTAL RESTORATIVE COMPONENTS

[76] Inventors: Fereidoun Daftary, 50 N. La Cienega Blvd., No. 206, Beverly Hills, Calif. 90211; Adriano Bracchetti, St. Gall Passarella 1, 20122 Milano, Italy

[21] Appl. No.: 991,969

[22] Filed: Dec. 17, 1992

[51] Int. Cl.⁵ ............................ A61C 3/00; B25B 13/00
[52] U.S. Cl. ........................... 433/163; 433/141; 81/124.3
[58] Field of Search ................ 433/141, 163, 173, 174; 81/124.3, 13

[56] References Cited

U.S. PATENT DOCUMENTS

| | | | |
|---|---|---|---|
| 518,328 | 4/1894 | Oakey | 81/124.3 X |
| 572,857 | 12/1896 | Barnes | 81/124.3 X |
| 2,574,156 | 11/1951 | Pechachek | 81/124.4 |
| 2,662,437 | 12/1953 | Reynolds | 81/124.3 |
| 4,520,697 | 6/1985 | Moetteli | 81/124.3 |
| 5,088,925 | 2/1992 | Mason | 433/141 |
| 5,129,823 | 7/1992 | Hughes | 433/141 |

*Primary Examiner*—John J. Wilson
*Assistant Examiner*—Nicholas D. Lucchesi
*Attorney, Agent, or Firm*—Thomas I. Rozsa; Tony D. Chen

[57] ABSTRACT

The present invention is a universal anatomical dental carrier for carrying a component of an anatomical dental restorative system which typically includes impression copings, healing caps, temporary and anatomic abutments, and screw bolts. The universal anatomical dental carrier comprises an elongated handle, a ring-shaped holder for press-fitting a generally cylindrical shaped portion of the anatomical dental restorative component, and a double-angled portion interconnecting the elongated handle and the ring-shaped holder to have the ring-shaped holder situated below and extended away from the elongated handle. The ring-shaped holder may incorporate an antifrictionally supported rotatable inner ring for press-fitting the generally cylindrical shaped portion of the anatomical dental restorative component, and the double-angled portion may incorporate a swivel joint for making the ring-shaped holder rotatable to any desired angle.

16 Claims, 3 Drawing Sheets

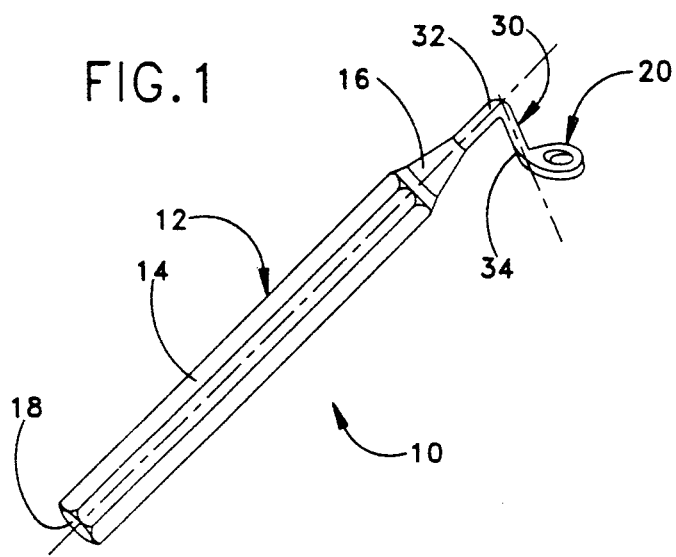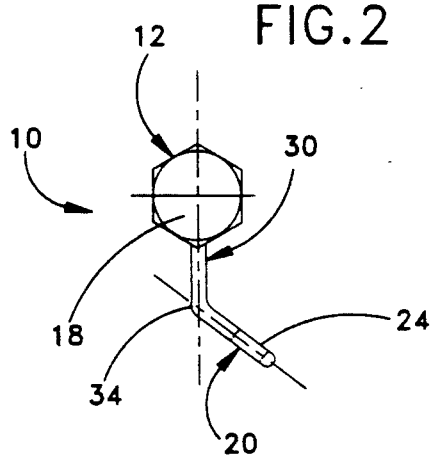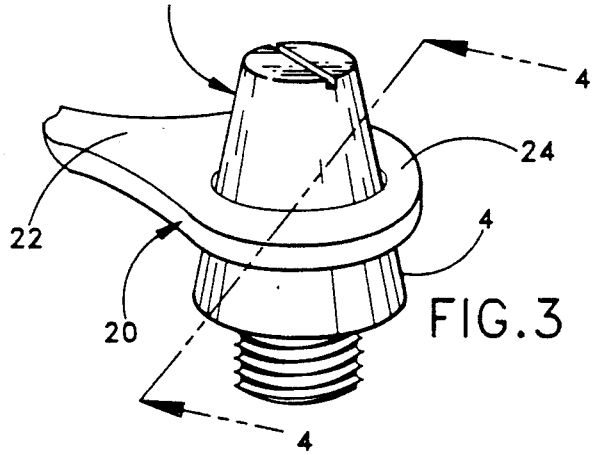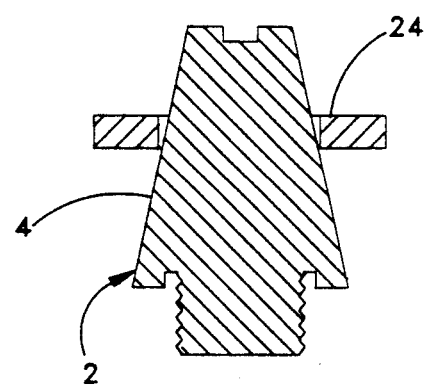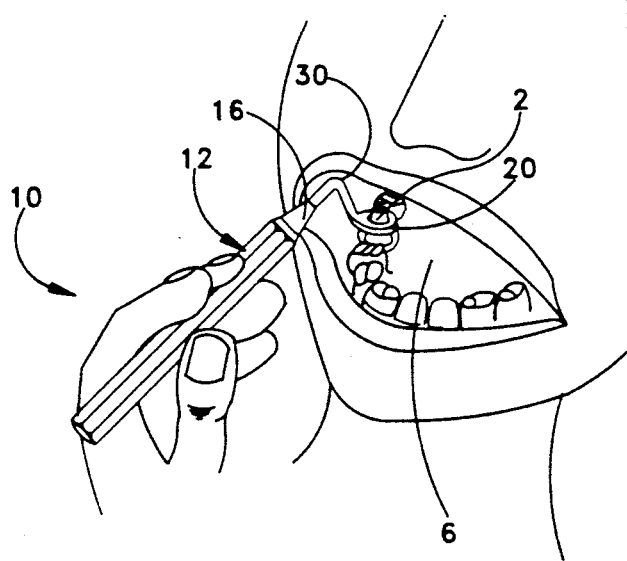

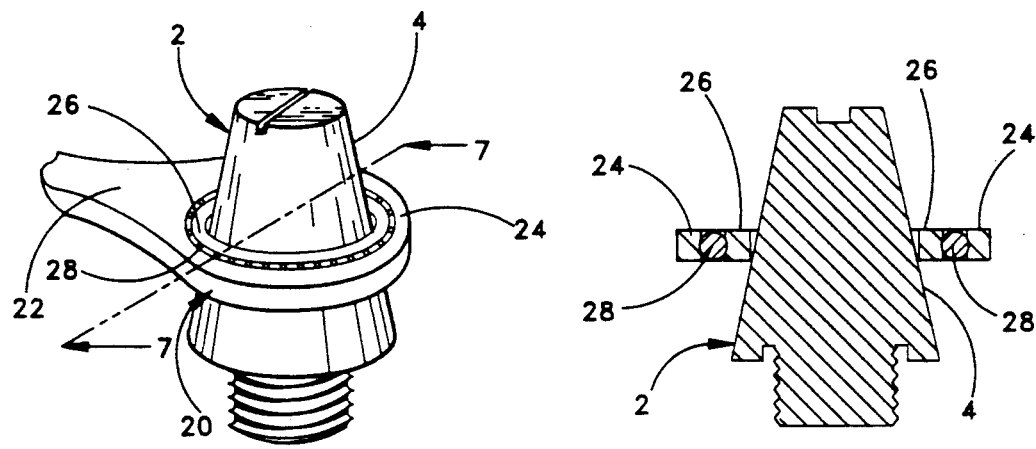
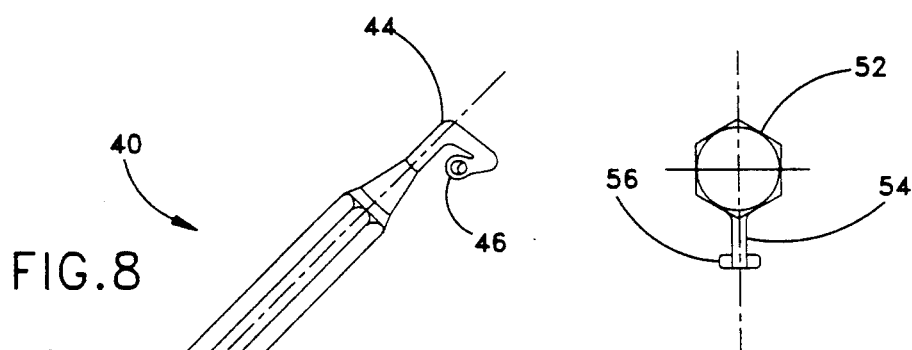
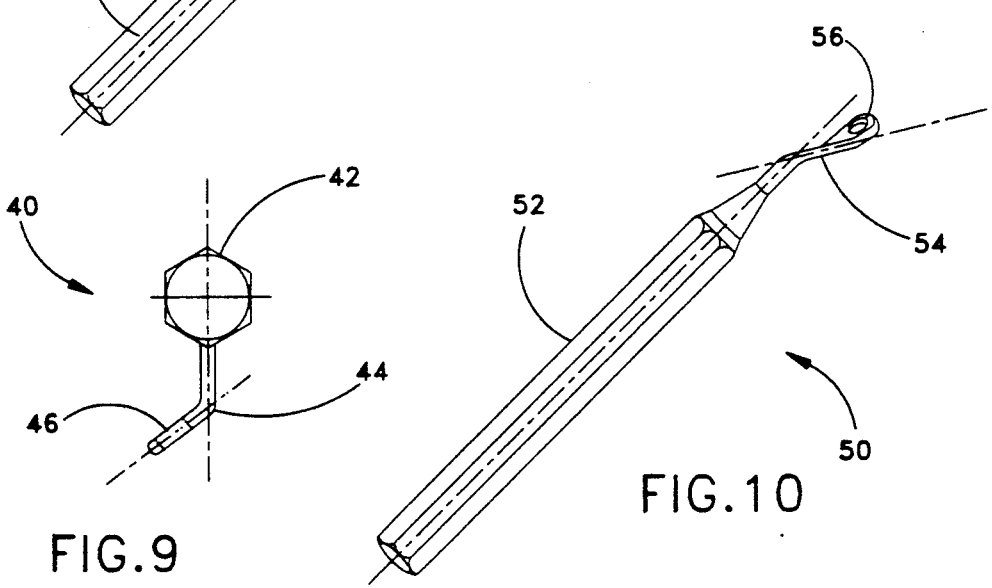

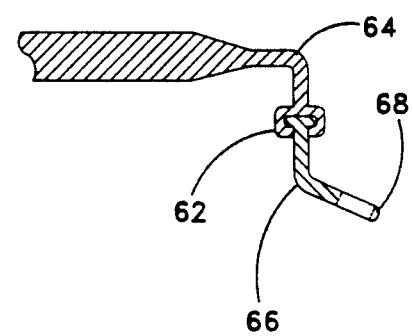
FIG.13
FIG.12
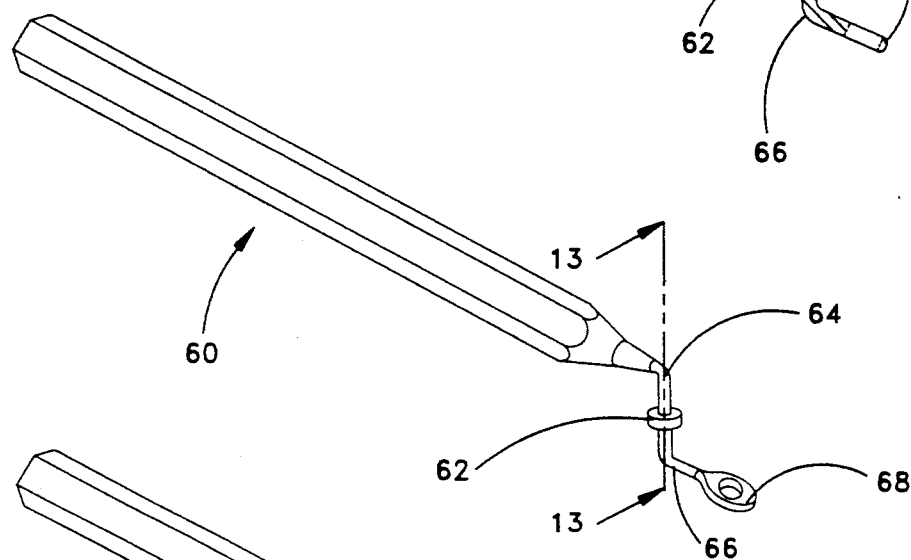
FIG.14
FIG.15
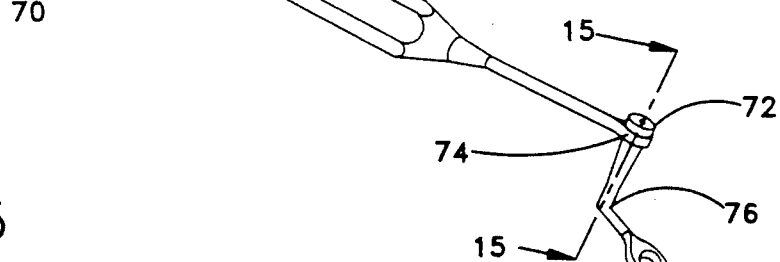
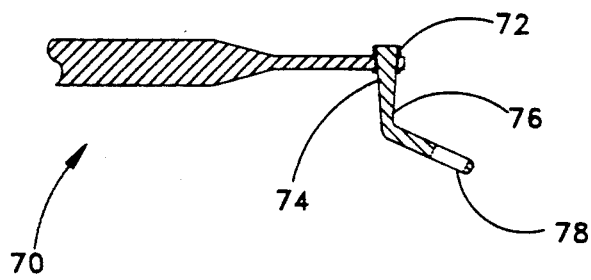

UNIVERSAL CARRIER FOR CARRYING VARIOUS ANATOMICAL DENTAL RESTORATIVE COMPONENTS

BACKGROUND OF THE INVENTION

1. Field of The Invention

The present invention relates to the field of medical instruments used in intraoral tooth prosthodontics restorations. More particularly the present invention relates to the field of dental tools for carrying various components of anatomical dental restorative systems used in intraoral tooth prosthodontics restorations.

2. Description of The Prior Art

Anatomical dental restorative systems are widely used in intraoral tooth prosthodontics restorations. The most often used components of a complete anatomical dental restorative system include implant fixtures, healing cap assemblies, impression coping assemblies, temporary and anatomic abutment assemblies, and screw bolts. Generally, a tooth prosthodontics restoration involves the following procedures.

The implant fixture is first installed into a socket prepared in the alveolus of the jawbone where a tooth has been extracted or otherwise lost. A cover screw is then used for sealing the top screw hole of the implant during the time the jaw bone is growing about the implant. After osseointegration of the implant, the gingiva is reopened and the cover screw is removed and replaced by a healing cap, which provides a predetermined contour to the re-healing gingival tissue.

After the re-opened gingival tissue has healed about the healing cap, the healing cap is removed so that an impression of the implant fixture and the surrounding gingival tissue can be made. The exposed end of the implant fixture typically has a hexagonal interface for defining the orientation of the attachment of a tooth analogue. The impression coping is attached to the implant fixture to make the impression for transferring to a working cast the natural dentition as well as both the exact position and the exact rotational alignment of the hexagonal interface of the implant fixture. Once the impression is made, it is removed from the patient's oral cavity and the impression coping is also removed. The impression coping is then attached to an analogue of the implant fixture and inserted back to the impression, and dental stone or die material is poured in to make the working cast for constructing the tooth analogue.

The temporary abutment can be fixed onto the implant fixture for supporting the tooth analogue, so the tooth analogue can be further finely finished to fit the actual contours of the patient's oral cavity. Finally, once everything is satisfactory, the completed tooth analogue can be permanently attached to the implant fixture by the anatomic abutment, and the intraoral tooth prosthodontics restoration is completed.

However, in intraoral tooth restoration operations, it is often very difficult to maneuver the various components of the anatomic dental implant system by hand. There are two main reasons for this difficulty. First, the sizes of the dental implant components, including impression copings, healing caps, temporary and anatomic abutments, and screw bolts, are very small. The overall length and maximum diameter of a typical dental implant component are both less than one centimeter. The small configurations of the dental implant components make them hard to handle. Second, the internal space of a patient's oral cavity is very limited, and frequently the location of the tooth restoration is hard to reach through the patient's mouth. The narrow space and limited access of the patients' oral cavity again makes it very difficult to handle the various dental components during an intraoral tooth restoration operation.

The small configuration of the anatomical dental restorative components and the limited access to the patients' oral cavities also make it easy to have an anatomical dental restorative component lost in a patient's oral cavity when the dentist tries to maneuver it within the patient's oral cavity, particularly when the tooth prosthodontics restoration is performed at a location adjacent the back of the patient's mouth.

It is therefore very desirable to have a carrying tool for intraoral tooth restoration operations, which tool can be used to maneuver a small anatomical dental restorative component inside a patient's oral cavity. There is no satisfactory tool which is specially designed to be used for this purpose.

SUMMARY OF THE INVENTION

The present invention is a universal carrier for carrying various components of anatomical dental restorative systems. Such anatomical dental restorative components usually include impression copings, healing caps, temporary and anatomic abutments, and screw bolts.

One of the inventors of the present invention, Fereidoun Daftary, is also the patentee of U.S. Pat. No. 5,035,619 issued on Jul. 30, 1991 (hereafter "the '619 Patent") and U.S. Pat. No. 5,073,111 issued on Dec. 17, 1991 (hereafter "the '111 Patent"). Daftary is also a joint applicant of U.S. patent application Ser. No. 07/782,091 filed on Oct. 24, 1991, which is going to be issued as U.S. Pat. No. 5,145,372 on Sep. 8, 1992 (hereafter "the '372 Patent"), and the applicant of U.S. patent application Ser. No. 07/896,613 filed on Jun. 10, 1992 (hereafter "the '613 Application"), now pending.

The '619 Patent, the '111 Patent and the '372 Patent have disclosed new anatomical dental restorative systems having unique healing cap assemblies and abutment assemblies, and their respective improved and reinforced embodiments. The '613 Application has disclosed a new impression coping assembly. In these inventions, the healing caps, the abutments and the impression copings are all configured with a top portion which is generally cylindrical in shape with a straight or slightly tapered sidewall. In fact, many components of other anatomical dental restorative systems are also configured with a top portion which is generally cylindrical in shape.

It has been discovered, according to the present invention, that if a tool has an elongated handle and a ring-shaped holder at its forward end, where a dentist can hold the elongated handle and press-fit the ring-shaped holder with the generally cylindrical shaped portion of an anatomical dental restorative component, then the tool becomes a universal carrier for holding an anatomical dental restorative component on its forward end so that the anatomical dental restorative component can be maneuvered within a patient's oral cavity.

It has also been discovered, according to the present invention, that if the ring-shaped holder of the universal carrier further has a ball bearing supported rotatable inner ring for press-fitting the anatomical dental restorative component, then an anatomical dental restorative component can be rotated by a driving tool for fastening purposes, while the anatomical dental restorative component is still being pressed and held in position by the universal carrier.

It has further been discovered, according to the present invention, that if the ring-shaped holder and the elongated handle of the universal carrying tool is connected by a double-angled portion, then the ring-shaped holder will be located below and extend away from the elongated handle, so that when the tool is used to carry an anatomical dental restorative component and place it into a patient's oral cavity, the handle can be used to move away the interior surface at the cheek of the patient's oral cavity to prevent the interior cheek from interfering with the placement of the anatomical dental restorative component.

It has additionally been discovered, according to the present invention, that if the double-angled portion of the universal carrier further includes a swivel joint, then the ring-shaped holder can be turned to any desired angle, so that the universal carrier can be used to maneuver an anatomical dental restorative component at any location inside a patient's oral cavity.

It is therefore an object of the present invention to provide a universal carrier for various anatomical dental restorative components, such as impression copings, healing caps, and temporary and anatomic abutments, where the universal carrier has an elongated handle and a ring-shaped holder at its forward end, such that a dentist can hold the elongated handle and press-fit the ring-shaped holder with the generally cylindrical shaped portion of an anatomical dental restorative component, so that the anatomical dental restorative component can be carried on the forward end of the universal carrier and maneuvered within a patient's oral cavity.

It is also an object of the present invention to provide a universal carrier for various anatomical dental restorative components, such as impression copings, healing caps, and temporary and anatomic abutments, where the ring-shaped holder of the universal carrier further has a ball bearing supported rotatable inner ring for press-fitting an anatomical dental restorative component, so that the anatomical dental restorative component can be rotated by a driving tool for fastening purposes, while the anatomical dental restorative component is still being pressed and held in position by the universal carrier.

It is a further object of the present invention to provide a universal carrier for various anatomical dental restorative components, such as impression copings, healing caps, and temporary and anatomic abutments, where the ring-shaped holder and the elongated handle of the universal carrying tool is connected by a double-angled portion, such that the ring-shaped holder will be located below and extend away from the elongated handle, so that when the tool is use to carry an anatomical dental restorative component into a patient's oral cavity, the handle can be used to move away the interior surface of the cheek of the patient's oral cavity to prevent the interior cheek from interfering with the placement of the anatomical dental restorative component.

It is an additional object of the present invention to provide a universal carrier for various anatomical dental restorative components, such as impression copings, healing caps, and temporary and anatomic abutments, where the double-angled portion of the universal carrier further includes a swivel joint, such that the ring-shaped holder can be turned to any desired angle, so that the universal carrier can be used to maneuver an anatomical dental restorative component at any location inside a patient's oral cavity.

The various embodiments of the present invention universal carrier include two different types: a fixed type and a swivel type. In the fixed type of embodiments, the interconnecting portion of the universal carrier is rigid, whereas in the swivel type of embodiments, the interconnecting portion of the universal carrier incorporates a swivel joint.

The fixed type of the present invention universal carrier generally comprises an elongated handle, a ring-shaped holder for press-fitting a generally cylindrical shaped portion of an anatomical dental restorative component, and a double-angled portion interconnecting the ring-shaped holder and the elongated handle for having the ring-shaped holder situated below and extending away from the elongated handle. The fixed type of the present invention universal carrier includes three different models: a right-side model, a left-side model and a center model.

The differences between the three models of the fixed type universal carriers concern the fixed extending direction of the ring-shaped holder relative to the elongated handle, as viewed from above and from the rear end of the elongated handle. In the right-side model the ring-shaped holder extends generally towards a fixed lower right-hand side direction, which is designed for handling an anatomical dental restorative component in the right-hand side region of a patient's oral cavity. In the left-side model the ring-shaped holder extends generally towards a fixed lower left-hand side direction, which is designed for handling the anatomical dental restorative component in the left-hand side region of the patient's oral cavity. Finally, in the center model the ring-shaped holder extends generally towards a fixed lower central direction, which is designed for handling the anatomical dental restorative component in the central region of the patient's oral cavity.

The swivel type embodiment of the present invention universal carrier generally comprises an elongated handle, a ring-shaped holder with an antifrictionally supported rotatable inner ring for press-fitting a generally cylindrical shaped portion of an anatomical dental restorative component, and a double-angled portion with a swivel joint interconnecting the ring-shaped holder and the elongated handle for having the ring-shaped holder situated below the elongated handle and to be rotatable into any angled orientation. The swivel joint may be located between the two angled points of the double-angled portion or at one of them.

Regardless of whether an embodiment of the present invention universal carrier is a fixed type or a swivel type, its ring-shaped holder may incorporate an antifrictionally supported rotatable inner ring for press-fitting the anatomical dental restorative component. The rotatable inner ring may be supported by a ball bearing or the like.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a perspective view of one embodiment of the present invention universal carrier of anatomical dental restorative components, showing the right-side model of the fixed type universal carrier.

FIG. 2 is a top plan view of the front portion of the right-side model of the fixed type universal carrier shown in FIG. 1.

FIG. 3 is a partial perspective view of the press-fit engagement of an anatomical dental restorative component and the ring-shaped holder of the universal carrier.

FIG. 4 is a cross-sectional view taken along line 4—4 in FIG. 3.

FIG. 5 is a perspective view showing how the present invention universal carrier is used to maneuver an anatomical dental restorative component within a patient's oral cavity in an intraoral tooth prosthodontics restoration.

FIG. 6 is a partial perspective view of the press-fit engagement of an anatomical dental restorative component and the ring-shaped holder of the universal carrier which further has ball bearing and a rotatable inner ring.

FIG. 7 is a cross-sectional view taken along line 7—7 in FIG. 5.

FIG. 8 is a perspective view of one embodiment of the present invention universal carrier of anatomical dental restorative components, showing the left-side model of the fixed type universal carrier.

FIG. 9 is a top plan view of the front portion of the left-side model of the fixed type universal carrier shown in FIG. 8.

FIG. 10 is a perspective view of one embodiment of the present invention universal carrier of anatomical dental restorative components, showing the center model of the fixed type universal carrier.

FIG. 11 is a top plan view of the front portion of the central model of the fixed type universal carrier shown in FIG. 10.

FIG. 12 is a perspective view of one embodiment of the present invention universal carrier of anatomical dental restorative components, illustrating the swivel joint located between the two angled points of the double-angled portion.

FIG. 13 is a partial cross-sectional view taken along line 13—13 in FIG. 12.

FIG. 14 is a perspective view of one embodiment of the present invention universal carrier of anatomical dental restorative components, illustrating the swivel joint located at one of the two angled points of the double-angled portion.

FIG. 15 is a partial cross-sectional view taken along line 15—15 in FIG. 14.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Referring to FIGS. 1 through 5, there is shown at 10 a perspective view of the present invention universal carrier for carrying a component of an anatomical dental restorative system. Throughout the drawings anatomic abutment 2 is shown as an example of the anatomical dental restorative component. Anatomic abutment 2 has a generally cylindrical shaped portion 4 with straight or slightly tapered sidewall. Of course many other anatomical dental restorative components, such as impression copings, healing caps, temporary abutments, and screw bolts, may also be carried by the universal carrier 10, since they also have similar generally cylindrical shaped portions.

The universal carrier 10 comprises a handle 12, which has an elongated body 14 with a tapered forward portion 16 and a rear end 18. The universal carrier 10 also comprises a holder 20, which has a tapered proximal portion 22 and a generally circular ring-shaped distal portion 24 for press-fitting the generally cylindrical shaped portion 4 of the anatomic abutment 2.

The universal carrier 10 further comprises a double-angled portion 30 which interconnects the tapered forward portion 16 of the handle 12 and the tapered proximal portion 22 of the holder 20. The double-angled portion 30 has two angled locations: a proximal angled location 32 and a distal angled location 34. At the proximal angled location 32 the double-angled portion 30 is bending downwardly, and at the distal angled location 34 the double-angled portion 30 is bending laterally. Therefore, the ring-shaped distal portion 24 of the holder 20 is situated below and extending away from the handle 12 at a fixed angle.

Since the ring-shaped distal portion 24 of the holder 20 extends away from the handle 12 at a fixed angle, the model shown in FIGS. 1 and 2 is a fixed type universal carrier. In this embodiment of the present invention, the universal carrier 10 is an unitary piece integrally formed by the handle 12, the double-angled portion 30 and the holder 20. The unitary universal carrier 10 may be made of any material suitable for intraoral tooth prosthodontics restorations.

Furthermore, the universal carrier 10 is a right-side model. As shown in FIG. 2, looking from the rear end 18 of the handle 12, the double-angled portion 30 of the universal carrier 10 is bending towards the right-hand side at the distal angled location 34. Accordingly the ring-shaped distal portion 24 of the holder 20 is situated below the handle 12 and extends along a direction generally towards the right-hand side. As shown in FIG. 5, this right-side model of the present invention universal carrier 10 is designed for handling the anatomic abutment 2 in the right-hand side region of a patient's oral cavity 6.

When the universal carrier 10 is used to carry the anatomic abutment 2 into the patient's oral cavity, the tapered forward portion 16 of the handle 12 and the double-angled portion 30 can serve as means for moving away the interior surface of the cheek of the patient's oral cavity 6 from the location of the implant fixture, so that the anatomic abutment 2 can be maneuvered therein without interference. In addition, since the ring-shaped holder 20 is situated below and extends away from the elongated handle 12 at an angle, the handle 12 and the double-angled portion 30 will not interfere with the existing teeth in the patient's oral cavity 6. Once the anatomic abutment 2 is carried to the desired location inside the patient's oral cavity 6, the universal carrier 10 can be further used to hold the anatomic abutment 2 in position, so it can be threadedly engaged with the implant fixture by using a driving tool.

As shown in FIGS. 6 and 7, the ring-shaped holder 20 of may further comprise a rotatable inner ring 26 supported by an antifrictional mechanism such as ball bearing 28 or the like. The anatomic abutment 2 can be press-fitted with the rotatable inner ring 26. The benefit of press-fitting the anatomic abutment 2 with the rotatable inner ring 26 is that, when the anatomic abutment 2 is held in position inside the patient's oral cavity 6 and threaded to the implant fixture, the ball bearing 28 supported inner ring 26 is also rotatable, which greatly reduces the resistance during threading of the anatomic abutment 2.

Referring to FIGS. 8 and 9, there is shown a left-side model 40 of the present invention universal carrier. Looking from the rear end of the handle 42, the double-angled portion 44 is being towards the left-hand side at its distal angled location. Accordingly the ring-shaped holder 46 is situated below the handle 42 and extends along a direction generally towards the left-hand side. This left-side model 40 of the present invention universal carrier is designed for handling an anatomical dental restorative component in the left-hand side region of a patient's oral cavity.

Referring to FIGS. 10 and 11, there is shown a center model 50 of the present invention universal carrier. Looking from the rear end of the handle 52, the double-angled portion 54 is bending towards a central direction at its distal angled location. Accordingly the ring-shaped holder 56 is situated below the handle 52 and extends along a direction generally towards the center. This center model 50 of the present invention universal carrier is designed for handling an anatomical dental restorative component in the central region of a patient's oral cavity.

The above described three models, the right-side model 10, the left-side model 40 and the center model 50, are fixed type embodiments of the present invention universal carrier. In these fixed type of embodiments, the interconnecting portion of the universal carrier is rigid, so that the angular relationship between the elongated handle and the ring-shaped holder is fixed. The ring-shaped holders of all three fixed models may incorporate the feature of the antifrictionally supported rotatable inner ring. When no rotatable inner ring is provided, a fixed type universal carrier can be made integrally as a unitary piece. When the feature of the rotatable inner ring is utilized, a fixed type universal carrier can still be made integrally as a unitary piece, with the addition of the ball bearing and the rotatable inner ring as separate pieces.

Referring to FIGS. 12 through 15, there is shown another type of the present invention universal carrier, with two different embodiments, which are the swivel type. In the swivel type of embodiments, the interconnecting double-angled portion of the universal carrier incorporates a swivel joint. In the embodiment 60 shown in FIGS. 12 and 13, the swivel joint 62 is positioned between the proximal angled location 64 and the distal angled location 66 of the double-angled portion. The ring-shaped holder 68 can be rotated to any desired angle. Alternatively, the swivel joint can be positioned at either the proximal angled location or the distal angled location of the double-angled portion. For example, in the embodiment 70 shown in FIGS. 14 and 15, the swivel joint 72 is positioned at the proximal angled location 74 of the double-angled portion 76. Again, the ring-shaped holder 78 can be rotated to any desired angle.

Since the ring-shaped holder of a swivel type universal carrier can be rotated to any desired angle relative to the elongated handle, the swivel type universal carrier can be used to maneuver an anatomical dental restorative component in either the right-hand or left-hand side region, or the central region of a patient's oral cavity. Therefore the present invention swivel type universal carriers give a dentist great flexibility in using the universal carrier. Furthermore, the feature of ball bearing supported rotatable inner ring shown in FIGS. 6 and 7 can also be incorporated into the ring-shaped holder of the swivel type universal carrier.

However, sometimes the simpler embodiment of the present invention universal carriers are still preferred. For example, sometimes an anatomical dental restorative component needs to be threaded to the dental implant fixture. The present invention universal carrier can be used to press-fit the anatomical dental restorative component, and then the anatomical dental restorative component can be rotated by swinging the handle of the universal carrier. When the universal carrier is used for this purpose, a fixed type universal carrier without rotatable inner ring at its ring-shaped holder is preferred, because the rotation of the handle needs to be transferred to the rotation of the anatomical dental restorative component.

The present invention has many advantageous features, including: (a) it provides a universal carrier for carrying various anatomical dental restorative components, such as impression copings, healing caps, temporary and anatomic abutments; (b) it also provides a universal carrier with a ring-shaped holder and an elongated handle interconnected by a double-angled portion, such that the ring-shaped holder is located below and extends away from the elongated handle, so that when the universal carrier is used to carry the anatomical dental restorative component into a patient's oral cavity, the handle can move away the interior surface of the patient's oral cavity to prevent the interior cheek from interfering with the operation; (c) it further provides a universal carrier with a ball bearing supported rotatable inner ring for press-fitting the anatomical dental restorative component, which allows the anatomical dental restorative component to be rotated by a driving tool for fastening purposes, while still being pressed and held in position by the universal carrier; and (d) it additionally provides a universal carrier with a swivel joint in the double-angled portion, such that the ring-shaped holder can be turned to any desired angle for maneuvering the anatomical dental restorative component at any location inside the patient's oral cavity.

Defined in detail, the present invention is a universal anatomical dental carrier for carrying a component of an anatomical dental restorative system which typically includes impression copings, healing caps, temporary and anatomic abutments, and screw bolts, the universal anatomical dental carrier comprising, (a) a handle having an elongated body with a tapered forward portion and a rear end; (b) a holder having a tapered proximal portion and a ring-shaped distal portion for press-fitting a generally cylindrical shaped portion of said anatomical dental restorative component; and (c) a double-angled portion interconnecting said forward portion of said handle and said proximal portion of said holder; (d) whereby said ring-shaped distal portion of said holder is situated below and extends away from said elongated body of said handle at a fixed angle.

Defined also in detail, the present invention is a universal anatomical dental carrier for carrying a component of an anatomical dental restorative system which typically includes impression copings, healing caps, temporary and anatomic abutments, and screw bolts, the universal anatomical dental carrier comprising, (a) a handle having an elongated body with a tapered forward portion and a rear end; (b) a holder having a tapered proximal portion and a ring-shaped distal portion with an antifrictionally supported rotatable inner ring for press-fitting a generally cylindrical shaped portion of said anatomical dental restorative component; and (c) a double-angled portion interconnecting said forward portion of said handle and said proximal portion of said holder; (d) whereby said ring-shaped distal portion of said holder is situated below and extends away from said elongated body of said handle at a fixed angle.

Defined again in detail, the present invention is a universal anatomical dental carrier for carrying a component of an anatomical dental restorative system which typically includes impression copings, healing caps, temporary and anatomic abutments, and screw bolts, the universal anatomical dental carrier comprising, (a) a handle having an elongated body with a tapered forward portion; (b) a holder having a tapered proximal portion and a ring-shaped distal portion for press-fitting a generally cylindrical shaped portion of said anatomical dental restorative component; and (c) a double-angled portion having a swivel joint and interconnecting said forward portion of said handle and said proximal portion of said holder; (d) whereby said ring-shaped distal portion of said holder is situated below said elongated body of said handle and is rotatable to extend away from said elongated body of said handle at any desired angle.

Defined further in detail, the present invention is a universal anatomical dental carrier for carrying a component of an anatomical dental restorative system which typically includes impression copings, healing caps, temporary and anatomic abutments, and screw bolts, the universal anatomical dental carrier comprising, (a) a handle having an elongated body with a tapered forward portion; (b) a holder having a tapered proximal portion and a ring-shaped distal portion with an antifrictionally supported rotatable inner ring for press-fitting a generally cylindrical shaped portion of said anatomical dental restorative component; and (c) a double-angled portion having a swivel joint and interconnecting said forward portion of said handle and said proximal portion of said holder; (d) whereby said ring-shaped distal portion of said holder is situated below said elongated body of said handle and is rotatable to extend away from said elongated body of said handle at any desired angle.

Defined broadly, the present invention is a universal dental carrier for carrying an anatomical dental restorative component, comprising, (a) an elongated handle portion; (b) a ring-shaped holder portion with an antifrictionally supported rotatable inner ring for press-fitting a generally cylindrical shaped portion of said anatomical dental restorative component; and (c) a double-angled portion interconnecting said elongated handle portion and said ring-shaped holder portion; (d) wherein said ring-shaped holder is situated below and extending away from said elongated handle at a fixed angle.

Defined also broadly, the present invention is a universal dental carrier for carrying an anatomical dental restorative component, comprising, (a) an elongated handle portion; (b) a ring-shaped holder portion for press-fitting a generally cylindrical shaped portion of said anatomical dental restorative component; and (c) a double-angled portion having a swivel joint and interconnecting said elongated handle portion and said ring-shaped holder portion; (d) whereby said ring-shaped holder portion is situated below said elongated handle portion and is rotatable to extend away from said elongated handle portion at any desired angle.

Defined more broadly, the present invention is a universal carrier comprising an elongated handle, a ring-shaped holder for press-fitting a generally cylindrical shaped portion of an anatomical dental restorative component, and a double-angled portion interconnecting the elongated handle and the ring-shaped holder for having the ring-shaped holder situated below and extended away from the elongated handle.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to show all of the various forms or modification in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A universal carrier comprising an elongated handle, a ring-shaped holder for press-fitting a generally cylindrical shaped portion of an anatomical dental restorative component, and a double-angled portion interconnecting the elongated handle and the ring-shaped holder for having the ring-shaped holder situated below and extended away from the elongated handle, wherein said ring-shaped holder incorporates an antifrictionally supported rotatable inner ring for press-fitting said generally cylindrical shaped portion of said anatomical dental restorative component.

2. The invention as defined in claim 1 wherein said rotatable inner ring of said holder is supported by a ball bearing mechanism.

3. A universal anatomical dental carrier for carrying a component of an anatomical dental restorative system which typically includes impression copings, healing caps, temporary and anatomic abutments, and screw bolts, the universal anatomical dental carrier comprising, a. a handle having an elongated body with a tapered forward portion and a rear end;
 b. a holder having a tapered proximal portion and a ring-shaped distal portion with an antifrictionally supported rotatable inner ring for press-fitting a generally cylindrical shaped portion of said anatomical dental restorative component; and
 c. a double-angled portion interconnection said forward portion of said handle and said proximal portion of said holder;

d. whereby said ring-shaped distal portion of said holder is situated below and extends away from said elongated body of said handle at a fixed angle.

4. The invention as defined in claim 3 wherein said ring-shaped distal portion of said holder extends generally towards a fixed lower right-hand side direction as viewed from above and said rear end of said handle for maneuvering said anatomical dental restorative component in a right-hand side region of a patient's oral cavity.

5. The invention as defined in claim 3 wherein said ring-shaped distal portion of said holder extends generally towards a fixed lower central direction as viewed from above and said rear end of said handle for maneuvering said anatomical dental restorative component in a central region of a patient's oral cavity.

6. The invention as defined in claim 3 wherein said ring-shaped distal portion of said holder extends generally towards a fixed lower left-hand side direction as viewed from above and said rear end of said handle for maneuvering said anatomical dental restorative component in a left-hand side region of a patient's oral cavity.

7. The invention as defined in claim 3 wherein said rotatable inner ring of said holder is supported by a ball bearing mechanism.

8. A universal anatomical dental carrier for carrying a component of an anatomical dental restorative system which typically includes impression copings, healing caps, temporary and anatomic abutments, and screw bolts, the universal anatomical dental carrier comprising,
   a. a handle having an elongated body with a tapered forward portion;
   b. a holder having a tapered proximal portion and a ring-shaped distal portion with an antifrictionally supported rotatable inner ring for press-fitting a generally cylindrical shaped portion of said anatomical dental restorative component; and
   c. a double-angled portion having a swivel joint and interconnecting said forward portion of said handle and said proximal portion of said holder;
   d. whereby said ring-shaped distal portion of said holder is situated below said elongated body of said handle and is rotatable to extend away from said elongated body of said handle at any desired angle.

9. The invention as defined in claim 8 wherein said swivel joint is situated between two angled locations of said double-angled portion.

10. The invention as defined in claim 8 wherein said swivel joint is situated at an angled location of said double-angled portion.

11. The invention as defined in claim 8 wherein said rotatable inner ring of said ring-shaped holder is supported by a ball bearing mechanism.

12. A universal dental carrier for carrying an anatomical dental restorative component, comprising,
   a. an elongated handle portion;
   b. a ring-shaped holder portion with an antifrictionally supported rotatable inner ring for press-fitting a generally cylindrical shaped portion of said anatomical dental restorative component; and
   c. a double-angled portion interconnecting said elongated handle portion and said ring-shaped holder portion;
   d. wherein said ring-shaped holder is situated below and extends away from said elongated handle at a fixed angle.

13. The invention as defined in claim 12 wherein said ring-shaped holder portion extends generally towards a fixed lower right-hand side direction, as viewed from a remote end of said elongated handle portion opposite to said ring-shaped holder portion, for maneuvering said anatomical dental restorative component in a right-hand side region of a patient's oral cavity.

14. The invention as defined in claim 12 wherein said ring-shaped holder portion extends generally towards a fixed lower central direction, as viewed from a remote end of said elongated handle portion opposite to said ring-shaped holder portion, for maneuvering said anatomical dental restorative component in a central region of a patient's oral cavity.

15. The invention as defined in claim 12 wherein said ring-shaped handle portion extends generally towards a fixed lower left-hand side direction, as viewed from a remote end of said elongated handle portion opposite to said ring-shaped holder portion, for maneuvering said anatomical dental restorative component in a left-hand side region of a patient's oral cavity.

16. The invention as defined in claim 12 wherein said rotatable inner ring of said holder portion is supported by a ball bearing mechanism.

* * * * *